(12) United States Patent
Krief

(10) Patent No.: US 9,844,951 B2
(45) Date of Patent: Dec. 19, 2017

(54) METHOD FOR MARKING A TRANSPARENT CONTAINER

(75) Inventor: Jérôme Krief, Vaulnaveys le Bas (FR)

(73) Assignee: Becton Dickinson France, Le Pont de Claix (FR)

( * ) Notice: Subject to any disclaimer, the term of this patent is extended or adjusted under 35 U.S.C. 154(b) by 561 days.

(21) Appl. No.: 13/695,172

(22) PCT Filed: Apr. 30, 2010

(86) PCT No.: PCT/IB2010/001425
§ 371 (c)(1),
(2), (4) Date: Jan. 9, 2013

(87) PCT Pub. No.: WO2011/135398
PCT Pub. Date: Nov. 3, 2011

(65) Prior Publication Data
US 2013/0120517 A1    May 16, 2013

(51) Int. Cl.
| | |
|---|---|
| *B41M 5/24* | (2006.01) |
| *B41M 5/26* | (2006.01) |
| *B41J 2/44* | (2006.01) |
| *A61M 5/31* | (2006.01) |
| *B41M 1/12* | (2006.01) |
| *B41M 1/40* | (2006.01) |
| *B41M 7/00* | (2006.01) |

(Continued)

(52) U.S. Cl.
CPC ............ *B41J 2/442* (2013.01); *A61M 5/3129* (2013.01); *B41M 1/12* (2013.01); *B41M 1/40* (2013.01); *B41M 5/24* (2013.01); *B41M 5/262* (2013.01); *B41M 7/009* (2013.01); *C03C 17/005* (2013.01); *C03C 23/0025* (2013.01); *A61J 2205/10* (2013.01); *A61M 2205/6072* (2013.01)

(58) Field of Classification Search
CPC .......... B41M 1/34; B41M 1/40; B41M 5/262; B41M 1/12; B41J 3/407; B41J 3/4073
See application file for complete search history.

(56) References Cited

U.S. PATENT DOCUMENTS 5,091,003 A * 2/1992 Boaz .......................... 106/31.05
5,908,721 A * 6/1999 Emoto et al. ..................... 430/7
(Continued)

FOREIGN PATENT DOCUMENTS

| DE | 19926878 A1 | 12/1999 |
| DE | 102006051373 A1 | 4/2008 |

(Continued)

OTHER PUBLICATIONS

Bassemir et al., "Inks", Kirk-Othmer Encyclopedia of Chemical Technology, 2004, pp. 1-28, vol. 14.

(Continued)

*Primary Examiner* — Kristal Feggins
*Assistant Examiner* — Kendrick Liu
(74) *Attorney, Agent, or Firm* — The Webb Law Firm

(57) ABSTRACT

The present invention relates to a method for marking a container comprising at least a transparent wall comprising the following steps:
  a) applying at least one spot of ink on an outer surface of said transparent wall,
  b) heating said transparent wall,
  c) engraving a data matrix in the spot of ink of said transparent wall. The invention also relates to a marked container and to a method for identifying such a marked container.

22 Claims, 2 Drawing Sheets

Figure 1:
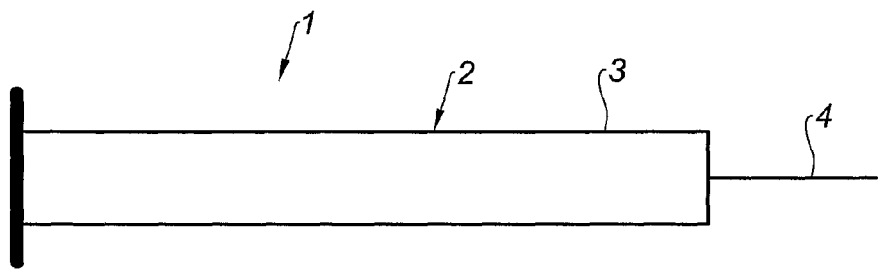

(51) Int. Cl.
*C03C 17/00* (2006.01)
*C03C 23/00* (2006.01)

(56) References Cited

U.S. PATENT DOCUMENTS

| | | | |
|---|---|---|---|
| 6,540,624 B1* | 4/2003 | Isogawa | 473/371 |
| 6,674,043 B2 | 1/2004 | Trinks et al. | |
| 2002/0102362 A1 | 8/2002 | Schneider | |
| 2002/0106309 A1* | 8/2002 | Mathus et al. | 422/102 |
| 2003/0039590 A1 | 2/2003 | Lodge | |
| 2004/0182475 A1 | 9/2004 | Vetter et al. | |
| 2005/0032262 A1* | 2/2005 | Yamanaka | 438/30 |
| 2005/0218126 A1* | 10/2005 | Leyvraz | 219/121.69 |
| 2007/0108288 A1* | 5/2007 | Caskey et al. | 235/462.08 |
| 2008/0034628 A1* | 2/2008 | Schnuckle | 40/310 |
| 2008/0210122 A1* | 9/2008 | Magdassi et al. | 106/31.05 |
| 2008/0304525 A1 | 12/2008 | Kupisiewicz et al. | |
| 2009/0188400 A1* | 7/2009 | Fleischle | B41M 5/24 101/129 |
| 2009/0305168 A1* | 12/2009 | Heley et al. | 430/315 |
| 2010/0108651 A1* | 5/2010 | Stahr | B41M 5/24 219/121.69 |

FOREIGN PATENT DOCUMENTS

| | | | |
|---|---|---|---|
| EP | 2157533 A1 | | 2/2010 |
| FR | 2893609 A3 | | 5/2007 |
| FR | 2927839 A1 | | 8/2009 |
| GB | 2401581 A | | 11/2004 |
| JP | 2004014169 A | * | 1/2004 |
| WO | 9805427 A1 | | 2/1998 |
| WO | 03/020527 A2 | | 3/2003 |
| WO | 2005032449 A1 | | 4/2005 |
| WO | 2006/117692 A1 | | 11/2006 |
| WO | 2006/123252 A1 | | 11/2006 |

OTHER PUBLICATIONS

DIN Deursches Institut fur Normung e.V., "Normenausschuss Informationstechnik", DIN EN ISO/IEC 15415, 2005, pp. 13-18 (E).

The Economist, "Reading bar codes with mobile phones: Snap it, click it, use it", Aug. 20, 2009, Seattle.

GS1 Healthcare—Position Statement, "GS1 Data Matrix", Oct. 7, 2009.

Marabuwerke GmbH & Co. KG, Tampapur TPU, Apr. 19, 2003, pp. 1-4, version 2.

Neuenschwander et al., "Practical guide to bar coding for patient medication safety", Am J Health-Syst Pharm, Apr. 15, 2003, pp. 768-779, vol. 60.

Wikipedia, "Pad printing", article accessed Aug. 5, 2015.
Wikipedia, "Test tube", article accessed Aug. 4, 2015.
Wikipedia, "Vitreous enamel", article accessed Jan. 18, 2016.

* cited by examiner

METHOD FOR MARKING A TRANSPARENT CONTAINER

The present invention relates to a method for marking a container having at least a transparent wall, such as containers for use in the medical field like syringe bodies. The invention also relates to the marked containers thus obtained and to a method for identifying such marked containers.

In the present application, the distal end of an article is to be understood as meaning the end furthest from the user's hand and the proximal end is to be understood as meaning the end closest to the user's hand when the article is in use. Likewise, in this application, the "distal direction" is to be understood as meaning the direction of injection, and the "proximal direction" is to be understood as meaning the opposite direction to the direction of injection.

Containers having at least a transparent wall, made of glass or plastic for example, are commonly used in the medical field. These containers may be any container used for the administration and/or the injection of medical products such as, for example, medicaments, and also any analytical, testing or diagnostic container. These containers may take the shape of a bottle, a syringe body, a vial or a tube, and they may be used to obtain an injection device, for example a syringe or an injection pen cartridge. These containers may be coated on one or more of their walls with a surface coating. These containers may also be filled with a substance, for example a medicament in divided or undivided solid, gel, powder or liquid form, in order to obtain an administration, for example injection, device, or a finished, ready-to-use, article for medical, testing, analytical or diagnostic use.

Because of their various uses and applications, and because of the various medicines they may contain, it is particularly important to determine exactly where a container comes from, what it contains, and to which use it is intended. Other information may be needed, in particular for a safe use of the container. It is also important that the information provided with said container may not be falsified. In this view, it is desirable to provide this information under the form of a mark, attached to the container, and containing the information needed. Indeed, marking a container is desirable for various purposes such as the following:

protection against copying or imitating the containers and/or the substance they may contain;
authentication of the original containers and of the substance they may contain;
traceability of the containers and of the substance they may contain, per batch or series, and possibly per unit; and
identification of the prefilled or not container, in the distribution chains and/or in use, in particular within a regulatory and/or security context regarding the origin of the container.

Various methods of marking and/or identifying a container have already been proposed. For example, it is known to identify various articles by external marking such as labelling, printing, etching or other techniques. These known methods have the drawback that the information supported by the marking may be modified, destroyed or damaged, removed or copied, falsified or altered, thereby making these methods of identification not very effective and not very useful, in particular for combating fraud and copies.

Other methods have been described, such as those providing the container with a marking obtained by modifying the substrate forming the wall of said container. For example, lasers are used for engraving information on a glass container.

For instance, it is known to engrave micro points with the help of a laser at the surface of a glass wall of a container. Nevertheless, such a marking method has the drawback of damaging the substrate, for instance the glass material, the container is made of: the engraving of the surface of the glass wall may actually cause microcracks at the place the micropoints are engraved, thereby weakening the glass wall of the container. Moreover, such a method may also generate glass micro-particles during the engraving step. In addition, once the marking is obtained, the information contained therein is not easily and rapidly readable. Indeed, the glass engraving implies a modification of the refractive index of the glass material at the location of the marking, thereby rendering the reading of the information difficult. In such cases, the marking must be read by transmission: such a reading step may be fastidious and time consuming.

It is also known to engrave information and/or data within the thickness of a glass wall of a container. Nevertheless, such a method requires the use of a femtosecond LASER and is very expensive.

One aspect of the present invention is to propose a method of providing a marking incorporated definitively at a surface of the substrate forming a transparent wall of a container without thereby significantly affecting the mechanical properties or characteristics, such as the impact strength for example, of the transparent wall of the container thus marked.

One aspect of the invention is to provide a method for marking a container comprising at least a transparent wall comprising the following steps:
a) applying at least one spot of ink on an outer surface of said transparent wall,
b) heating said transparent wall,
c) engraving a data matrix in the spot of ink of said transparent wall.

By "transparent" material is meant according to the present application, a material allowing at least 5% of light transmission in the visible, preferably allowing at least 50% of light transmission in the visible, and more preferably allowing at least 90% of light transmission in the visible. As an example, glass usually allows at least 90% of light transmission in the visible. For example, opalescent materials, which allow at least 5% of light transmission in the visible, for example at least 50% of light transmission in the visible, may be used in the present invention. Translucent materials, which allow the diffusion of a certain percentage of the light they receive, and which also allow at least 5% of light transmission in the visible, for example at least 50% of light transmission in the visible, may also be used in the present invention. Opalescent materials and translucent materials are therefore comprised in the term "transparent" according to the present application.

For example, said transparent wall is selected from glass walls, polyolefin walls, polycarbonate walls and combinations thereof.

The method of the invention allows preserving the integrity of the material forming the transparent wall of the container that is marked. Indeed, with the method of the invention, it is the ink spot that is engraved, not the substrate forming the transparent wall of the container to be marked. As a result, the substrate forming the transparent wall of the container is not affected by the marking process. The marking is provided at the surface of the container without any risk of damaging the structure of the container. In particular, in the case where the transparent wall of the container is made of glass, there is neither risk to cause microcracks in said glass wall nor to generate micro-particles of glass. The glass wall is not affected by the engraving step of the ink spot.

Moreover, the marking provided by the method of the invention is resistant and long lasting. With the marking method of the invention, the information supported by the marking may not be modified, destroyed or damaged, removed or copied, falsified or altered.

In addition, the method of the invention is cost effective: it does not require the use of high performance laser, such as a femtosecond LASER.

In an embodiment of the method of the invention, the application of step a) is performed via tampography. For example, in an embodiment, in step b), said transparent wall is heated at a temperature ranging from 55 to 65° C., preferably at about 60° C., for a time period ranging from about 6 to 8 minutes, preferably about 7 minutes.

In another method of the invention, the application of step a) is performed via serigraphy. For example, in an embodiment, in step b), said transparent wall is heated at a temperature ranging from 625 to 660° C., preferably at about 650° C., for a time period ranging from about 3 to 22 minutes, preferably about 5 minutes.

In embodiments, the engraving step c) is performed with a LASER.

In embodiments, the method further comprises a step d), subsequent to step c), during which the ink remaining around the data matrix is removed. For example, the removing of step d) may be performed with a LASER.

Another aspect of the invention is a marked container obtained according to the method described above.

As seen above, such a marked container is provided with reliable data and information that may not be copied or altered. In addition, the marked container of the invention preserves its integrity, and its mechanical properties are not altered by the marking method described above. The marked container of the invention may be prefilled before the marking process. There is no risk that the substance contained therein be altered, damaged or modified by the marking method of the invention.

The marked container of the invention may further be submitted to treatments requiring specific conditions of temperature and pressure, such as sterilisation treatment, without any risk that the marking be altered.

The marked container of the invention may be prefilled with a substance. In embodiments, said transparent wall is made of glass. The marked container may be a syringe body, for example provided with a needle.

Another aspect of the invention is a method for identifying a marked container as described above, comprising the following steps:
  illuminating with a light source the data matrix engraved in the ink spot of said transparent wall,
  reading the information contained in the data matrix by means of a camera capturing the reflected light emitted by the data matrix.

The indentifying method of the invention is easy to perform. In particular, because the material forming the transparent wall of the container is not altered by the marking method of the invention, it is possible to read the information supported by the marking by reflection of a light previously directed to said marking. As a consequence, the reading step may be completed very rapidly. Moreover, the reading step may also be efficiently performed, even if the container is filled with a substance, whatever the nature of that substance: in particular, this substance may not be transparent. Thanks to the marking method of the invention, the data matrix engraved is particularly visible and the reading step is therefore facilitated.

The identifying method of the invention allows for example the identification of more than 18,000 marked containers per hour. Such a method is therefore particularly advantageous in chain assembly lines.

Figure 2:
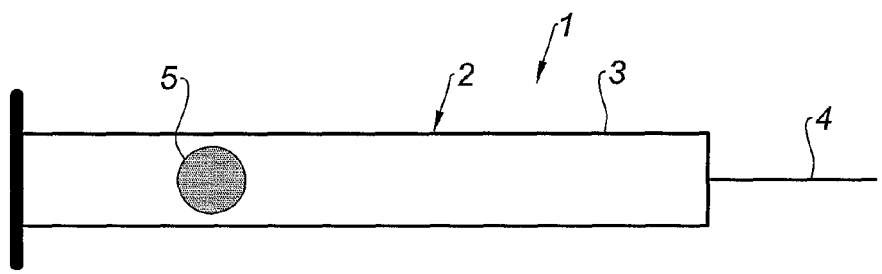
Figure 3:
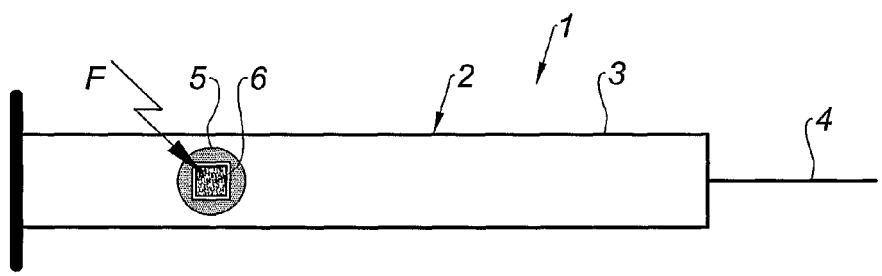
Figure 4:
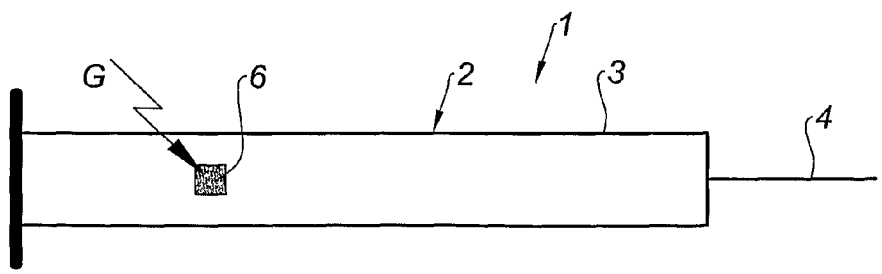
Figure 5:
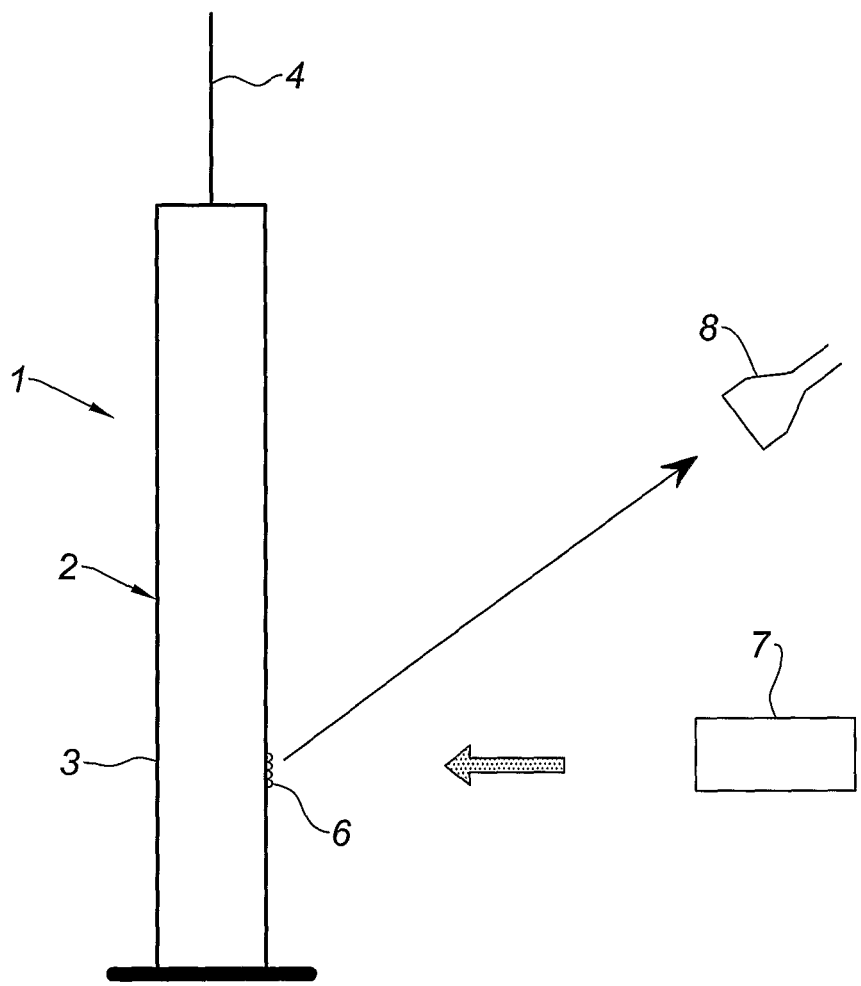

The methods of the invention and marked container of the invention will now be further described in reference to the following description and attached drawings in which:

FIG. 1 is a side view of a container intended to be marked according to the method of the invention, FIG. 2 is a side view of the container of FIG. 1 having undergone step a) of the marking method of the invention, FIG. 3 is a schematic view of step c) of the marking method of the invention, FIG. 4 is a schematic view of optional step d) of the marking method of the invention, FIG. 5 is a schematic view illustrating the identifying method of the invention.

With reference to FIG. 1 is described a container, under the form of a syringe body 1 comprising a tubular barrel 2 having a transparent wall 3. As defined above, "transparent" means herein that the wall 3 is made of a material allowing at least 5% of light transmission in the visible, preferably allowing at least 50% of light transmission in the visible, and more preferably allowing at least 90% of light transmission in the visible. For example, the tubular barrel may be made of glass material or of plastic material, such as polyolefin, polycarbonate or mixtures thereof. The syringe body 1 shown on FIG. 1 is not prefilled. In embodiments not shown, the syringe body is prefilled with a medical substance and this medical substance may not be transparent. The syringe body 1 is provided at its distal end with a needle 4.

In embodiments not shown, the container could be a cartridge, a vial, a bottle, a tube such as a catheter, or other known or hereafter developed articles suitable for containing a drug substance.

A first step of the marking method of the invention is to apply a spot of ink on an outer surface of the transparent wall 3. By "outer" surface is meant that the spot of ink is not engraved in the thickness of the wall 3 and does not penetrate the thickness of the wall on which it is applied, but is applied on the surface of the wall.

By "ink" is meant according to the present application a printing ink. The ink used is for example all inks suitable for tampography or serigraphy. In particular, the ink used in the method of present invention is water resistant and is suitable for being printed on glass materials.

The spot of ink may have any shape: for example it can be a round spot or a square or rectangle spot. The size of the spot of ink is function of the size of the data matrix desired to be engraved therein. For instance, the spot of ink may be a round spot of 3 mm diameter. The spot of ink is usually full (no voids) and printed in dark color, such as black.

In an embodiment of the method of the invention, the spot of ink is applied on the outer surface of the transparent wall via tampography. Such a technique is well known from persons of skill in the art and will not be described in great details herein. Basically, in such a technique, an inking pad is used, which is dripped into an ink reservoir and the inking pad is then applied on the surface to be printed. For example, one can use tampography machines provided by companies Thermofla, Febvre, Cartolux or Sisma.

In such an embodiment, the transparent wall, provided with the spot of ink is then heated at a temperature ranging from 55 to 65° C. for a time period ranging from about 6 to 8 minutes. Such a step allows the fixing and the curing of the ink. For example, the transparent wall is heated at a temperature of 60° C. for about 7 minutes. Such a technique allows in particular marking a container such as a syringe body having a needle assembled by glue. Indeed, the relatively low temperature (around 60° C.) at which the heating step is conducted does not affect adhesion of the needle for a syringe in which the needle is secured by an adhesive.

In an alternative embodiment of the method of the invention, the spot of ink is applied via serigraphy, also called screen printing. Such a technique is well known from persons of skill in the art and will not be described in great details herein. Basically, in such a technique, stencils or screens are used to protect the parts of a surface that should not receive ink and the ink is projected on the parts not protected by a screen.

In such an embodiment, the transparent wall, provided with the spot of ink is then heated at a temperature ranging from 625 to 666° C. for a time period ranging from about 3 to 22 minutes. Such a step allows the fixing and the curing of the ink. For example, the transparent wall is heated at a temperature of 650° C. for about 5 minutes.

On FIG. 2 is shown the syringe body 1 of FIG. 1 having the spot of ink 5 applied on an outer surface of its transparent wall 3.

In a third step (step c)) of the marking method of the invention, a data matrix 6 is engraved in the spot of ink 5, as shown on FIG. 3. The engraving is usually performed with a LASER, materialized on FIG. 3 by arrow F. The engraving consists in removing parts of the ink of the ink spot in order to create white parts (squares, bars), defined by the parts of the surface of the transparent wall 3 thus left visible, thereby creating a two dimensional barcode print which will form the data matrix 6. It will then be possible to read a black data matrix on a white background, the white background being the outer surface of the transparent wall 3, within the limits of the ink spot 5. During the engraving step, the LASER is used at such a frequency that the integrity of the transparent wall 3 is not affected. One skilled in the art knows how to determine which frequency of the LASER should be used so that the thickness of the transparent wall 3 is not attacked by the LASER. The engraving has therefore no influence, no effect on the transparent wall. Only the ink of the spot of ink is affected by the engraving. In particular, in the case where the transparent wall 3 of the container is made of glass, there is neither risk to cause microcracks in said glass wall nor to generate micro-particles of glass.

During the engraving step, such information as batch number, manufacturing date, manufacturing components, identification number, nature of substance contained, graduations, expiration date, etc. may be "engraved" within the data matrix.

After the engraving step, the syringe body 1 is marked: thanks to the engraved data matrix 6, the syringe body 1 is provided with reliable data and information that may not be copied or altered. In addition, the marked syringe body 1 preserves its integrity, and its mechanical properties are not altered by the marking method described above. The marked container of the invention may be prefilled before the marking process. There is no risk that the substance contained therein be altered, damaged or modified by the marking method of the invention.

The marked container 1 of the invention may further be submitted to treatments requiring specific conditions of temperature and pressure, such as sterilisation treatment, without any risk that the marking be altered.

In an optional additional step (step d)), the ink remaining around the data matrix 6 may be removed from the outer surface of the transparent wall 3, for example by means of a LASER, as shown on FIG. 4, on which the LASER is materialized by arrow G.

One skilled in the art knows how to determine which frequency of the LASER should be used to remove the remaining ink so that the thickness of the transparent wall 3 is not attacked by the LASER and without damaging the engraved data matrix 6. The step of removing the remaining ink has therefore no influence, no effect on the transparent wall. Only the remaining ink of the spot of ink which is located around the data matrix 6 is affected by the present step. In particular, in the case where the transparent wall 3 of the container is made of glass, there is neither risk to cause microcracks in said glass wall nor to generate micro-particles of glass.

With reference to FIG. 5 is illustrated the identifying method of the invention. The marked syringe body 1, i.e. provided with the data matrix 6 marked as described in reference to FIGS. 1-4, is illuminated by a light source 7. The data matrix 6 is therefore illuminated by the light source 7 and it reflects a part of this light: this reflected light emitted by the illuminated data matrix 6 is captured by a camera 8 and may be further analysed, for example by a suitable software of a computer, so as to retrieve the information and data contained in the data matrix 6.

The indentifying method of the invention is easy to perform, in particular, because the material forming the transparent wall of the container or syringe body is not altered by the marking method of the invention. In particular, because the refractive index of the transparent wall 3 is not affected by the marking method of the present invention, the information contained in the data matrix may be read simply by reflection of a light projected on said data matrix. As a consequence, the reading step may be completed very rapidly. Moreover, the reading step may also be efficiently performed, even if the container or syringe body is filled by a substance, whatever the nature of that substance: in particular, this substance may not be transparent. Thanks to the marking method of the invention, the data matrix engraved is particularly visible and the reading step is therefore facilitated.

The identifying method of the invention allows the identification of more than 18,000 marked containers per hour. Such a method is therefore particularly advantageous in chain assembly lines.

The invention claimed is:

1. A method for marking a container comprising at least a transparent wall comprising the following steps:
    a) applying at least one spot of ink directly onto an outer surface of said transparent wall,
    b) heating said transparent wall onto which the at least one spot of ink has been applied at a temperature and a time period sufficient to cure the ink to fix the ink onto the wall, then,
    c) engraving a data matrix in the spot of ink of said transparent wall, wherein the data matrix includes at least one of data or information.

2. A method according to claim 1 wherein the application of step a) is performed via tampography.

3. A method according to claim 2, wherein in step b), said transparent wall is heated at a temperature ranging from 55 to 65° C., for a time period ranging from about 6 to 8 minutes.

4. A method according to claim 3, wherein in step b), said transparent wall is heated at a temperature preferably at about 60° C., for a time period of about 7 minutes.

5. A method according to claim 1, wherein the application of step a) is performed via serigraphy.

6. A method according to claim 5, wherein in step b), said transparent wall is heated at a temperature ranging from 625 to 660° C., for a time period ranging from about 3 to 22 minutes.

7. A method according to claim 6, wherein in step b), said transparent wall is heated at a temperature preferably at about 650° C., for a time period of about 5 minutes.

8. A method according to claim 1, wherein the engraving step c) is performed with a LASER.

9. A method according to claim 8, wherein the LASER comprises a frequency which has no effect on the transparent wall.

10. A method according to claim 1, further comprising a step d), subsequent to step c), during which the ink remaining around the data matrix is removed.

11. A method according to claim 10, wherein the removing of step d) is performed with a LASER.

12. A marked container obtained by a method according to claim 1.

13. A marked container according to claim 12, wherein said container is prefilled with a substance.

14. A marked container according to claim 12, wherein said transparent wall is made of glass.

15. A marked container according to claim 12, wherein said container is a syringe body.

16. A marked container according to claim 15, wherein said syringe body is provided with a needle.

17. A method for identifying a marked container according to claim 12, comprising the following steps:
   illuminating with a light source the data matrix engraved in the ink spot of said transparent wall,
   reading the information contained in the data matrix by means of a camera capturing the reflected light emitted by the data matrix.

18. A method according to claim 1, wherein the at least one of data or information includes data or information related to the container or contents of the container.

19. A method according to claim 1, wherein the data matrix comprises an opaque data matrix on said transparent wall.

20. A method according to claim 1, wherein the step of engraving is applied directly to the ink at the surface of the container.

21. A method for marking a container comprising at least a transparent wall comprising the following steps:
   a) applying at least one spot of ink directly onto an outer surface of said transparent wall via tampography,
   b) heating said transparent wall onto which the at least one spot of ink has been applied at a temperature ranging from 55 to 65° C., for a time period ranging from about 6 to 8 minutes to cure the ink and fix the ink onto the wall, then,
   c) engraving a data matrix in the spot of ink of said transparent wall, wherein the data matrix includes at least one of data or information.

22. A method for marking a container comprising at least a transparent wall comprising the following steps:
   a) applying at least one spot of ink directly onto an outer surface of said transparent wall via serigraphy,
   b) heating said transparent wall onto which the at least one spot of ink has been applied at a temperature ranging from 625 to 660° C., for a time period ranging from about 3 to 22 minutes to cure the ink and fix the ink onto the wall, then,
   c) engraving a data matrix in the spot of ink of said transparent wall, wherein the data matrix includes at least one of data or information.

* * * * *